(12) United States Patent
Honey et al.

(10) Patent No.: US 6,764,499 B2
(45) Date of Patent: Jul. 20, 2004

(54) MEDICAL DEVICE HANDLE

(75) Inventors: R. John D'A. Honey, Toronto (CA); Marvin O. Andrews, Bloomington, IN (US); Frank J. Fischer, Jr., Bloomington, IN (US); John H. Ward, Spencer, IN (US)

(73) Assignee: Cook Urological Incorporated, Spencer, IN (US)

( * ) Notice: Subject to any disclaimer, the term of this patent is extended or adjusted under 35 U.S.C. 154(b) by 344 days.

(21) Appl. No.: 09/861,309

(22) Filed: May 18, 2001

(65) Prior Publication Data

US 2002/0026202 A1 Feb. 28, 2002

Related U.S. Application Data

(60) Provisional application No. 60/205,193, filed on May 18, 2000.

(51) Int. Cl.[7] .............................................. A61B 17/28
(52) U.S. Cl. ...................... 606/207; 606/206; 606/126; 606/127; 600/104
(58) Field of Search ................................ 606/207, 170, 606/41, 206, 126, 127, 128, 113, 114, 115, 171, 174, 200, 1; 81/487; 600/104–108

(56) References Cited

U.S. PATENT DOCUMENTS 5,159,861 A    11/1992  Anderson
5,456,683 A *  10/1995  Fritzch et al. ................. 606/41
5,792,165 A     8/1998  Klieman et al.
6,053,934 A *   4/2000  Andrews et al. ............. 606/207

* cited by examiner

Primary Examiner—Henry Bennett
Assistant Examiner—Kathryn Odland
(74) Attorney, Agent, or Firm—Brinks Hofer Gilson & Lione

(57) ABSTRACT

A replaceable handle for side loading the proximal end of a medical device therein, which is typically inserted with the operating lumen of an endoscope. The replaceable handle can side-load the proximal end of the device into the handle for added manipulation of the distal end such as in removing a stone from the kidney or ureter leading therefrom. An inner housing is rotatable within an outer housing of the handle to secure the medical device in the housing passageway, and is spring biased to then move proximally with respect to the outer housing, moving the inner control rod of the medical device proximally to withdraw the stone basket mostly into the outer cannula and capture the stone for removal from the patient. A push button in the proximal end portion of the inner housing is depressible to permit insertion or withdrawal of the proximal end of the inner control rod of the stone retriever within the inner housing, and is releasable to secure the inner control rod in the handle.

15 Claims, 6 Drawing Sheets

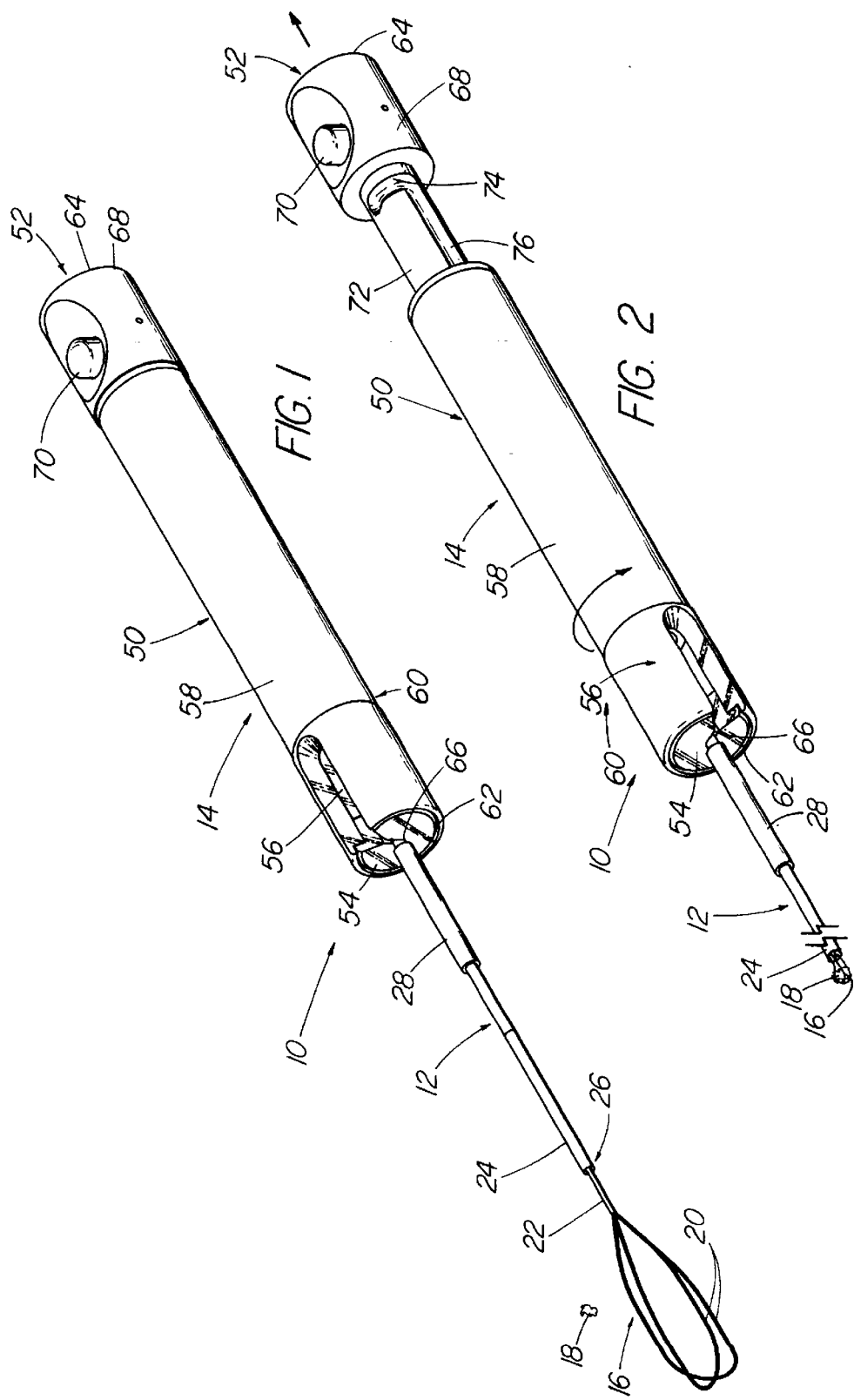

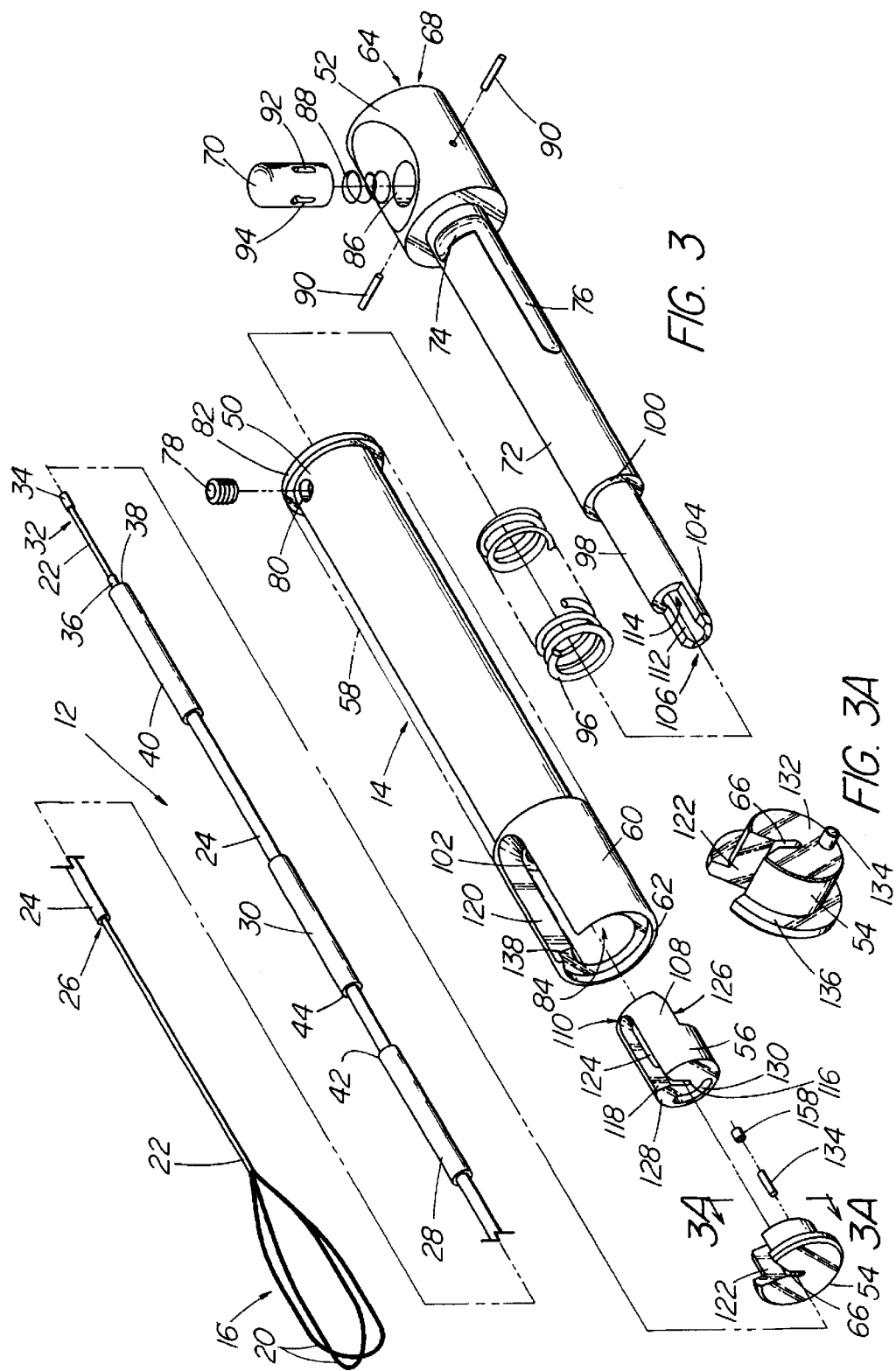

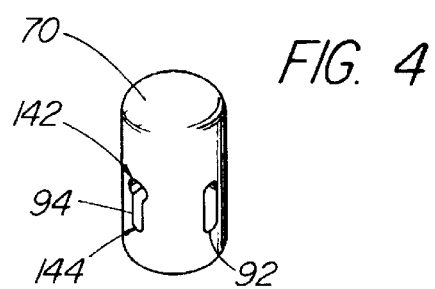
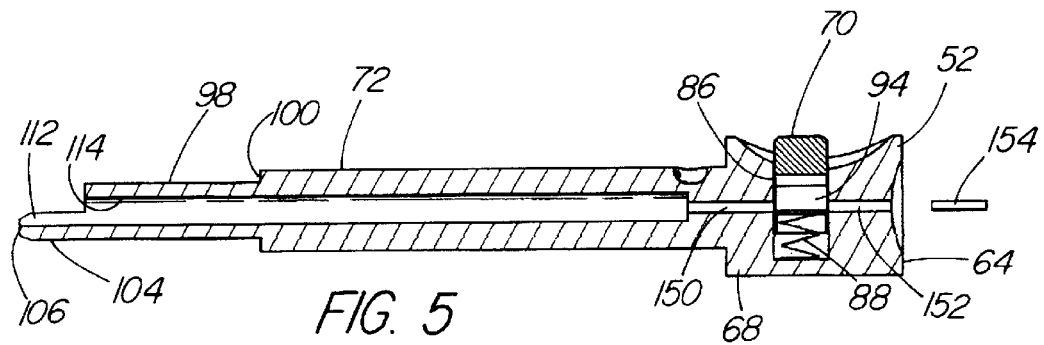
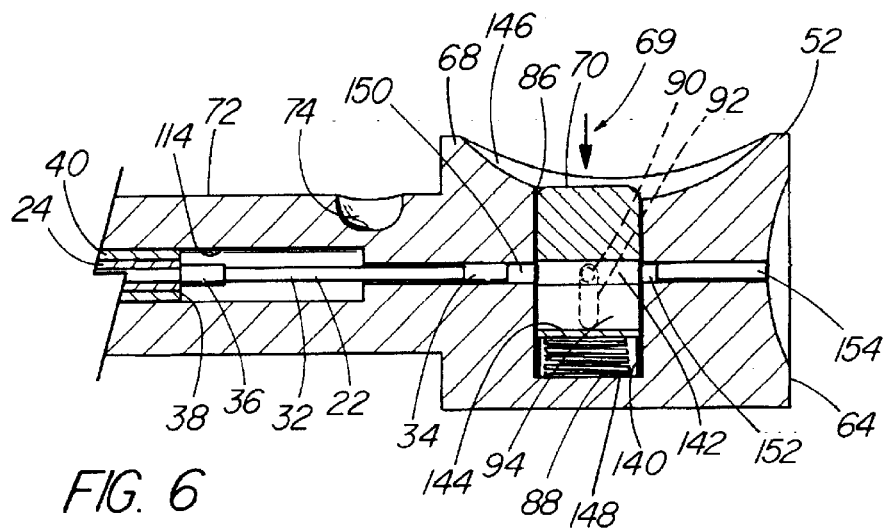

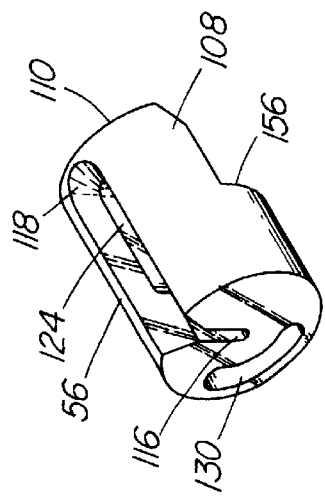
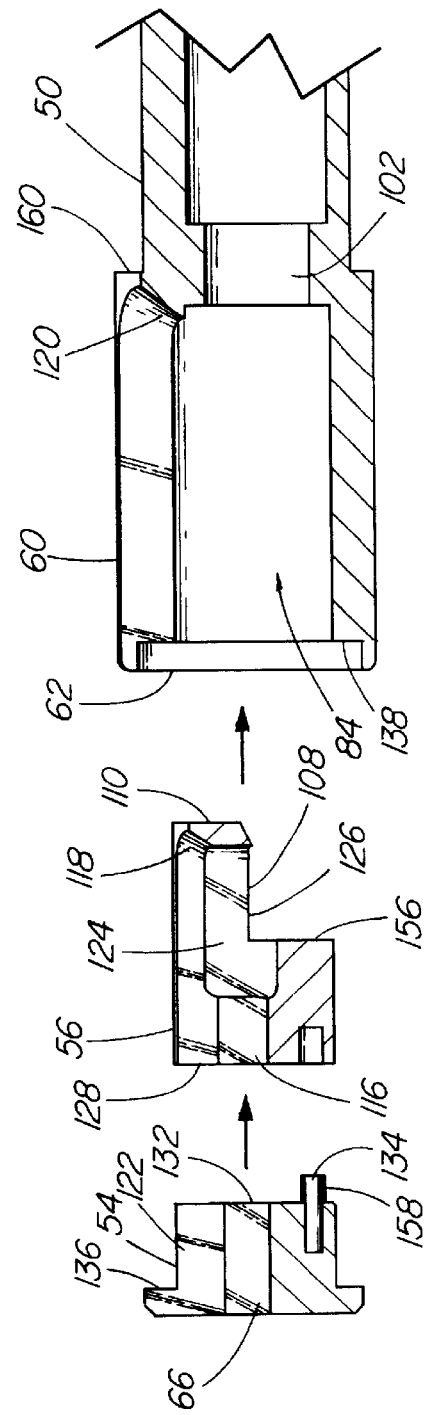

MEDICAL DEVICE HANDLE

CROSS-REFERENCE TO RELATED APPLICATION

This application claims priority of provisional application Serial No. 60/205,193 filed May 18, 2000.

TECHNICAL FIELD

This invention relates generally to medical devices and, in particular, to a handle for positioning thereinto the proximal end of a medical device for controlled movement with respect thereto.

BACKGROUND OF THE INVENTION

Extractors or baskets have been used for the removal of stones and other foreign objects from the urinary or biliary system. Often, the distal portion of these devices consist of a series of wires or strips that can be manipulated by the handle and actuating wire to expand to form an open basket. By further manipulating the handle of the extractor, the target object is captured within the basket, and the device is withdrawn from the body.

The procedure for extraction of a kidney stone usually requires that an endoscope be introduced to locate the obstruction. Once the stone is visualized, the basket or extractor is introduced through an operating lumen in the scope to complete the procedure. Occasionally, the extractor with the stone are too large to be safely withdrawn and further instrumentation such as forceps or an ultrasonic wire must be introduced that aid in fragmenting the object for removal. Without an additional operating lumen through which these instruments may be introduced, the endoscope must be withdrawn over the extractor. To accomplish this, the handle of the extractor must first be removed.

Handles for many current extractors are end loaded with a hub or expanded portion at the proximal end of the actuating wires. The hubs locks into place with the handle mechanism. Unfortunately, however, they must be cut off the proximal end of the wire before the endoscope can be slid off the end of the extractor. This prevents reattachment and reuse of the handle to complete the procedure once the basket has been freed. The ideal handle for a stone extractor must be able to be removed on a temporary basis and be easily reattached without the loss of handle function.

One such handle for a stone extractor or retriever is disclosed in U.S. Pat. No. 6,053,934 issued to Andrews, et al., the disclosure of which is hereby incorporated by reference. The handle is disclosed for side loading the proximal end of a medical device therein, which is typically inserted within the operative lumen of an endoscope. The handle is easily removed from the proximal end of the medical device for removing the endoscope over the device. With the endoscope removed, the replaceable handle can side-load the proximal end of the device for added manipulation of the distal end such as in removing a stone from the kidney or ureter leading therefrom. Having an inner housing therewithin, the outer housing also includes a first attachment mechanism disposed about the distal end for receipt of the first device while the inner housing includes a second attachment mechanism in communication with an inner passageway for receipt of a second device adjacent to the first member. The outer housing also includes a projection positionable into the positioning channel of the inner elongated member to control longitudinal and rotational movement therebetween. The inner housing is longitudinally slidable in the handle passage when the projection is positioned in a longitudinal component of the positioning channel. The inner housing is also rotatable in the handle passage when the projection is positioned in a transverse or circumferential component of the positioning channel. Removing a stone with the retriever requires holding the inner housing firmly in the proximal-most position along the outer housing with one hand, while simultaneously pulling the retriever proximally from the patient with the other hand, or by another person assisting the procedure.

It is desired to provide a handle that facilitates manipulation of the inner device to perform a work step, such as grasping a stone prior to removal, by applying tension in only one direction needing only one hand.

It is also desired to provide a handle that enables easy removal and insertion of a medical device with respect to the handle.

SUMMARY OF THE INVENTION

The foregoing problems are solved and a technical advance is achieved in an illustrative replaceable or removable handle for a medical device that is typically inserted through the operating lumen of an endoscope, where the medical device includes an outer member and an inner member that is to be operable axially with respect to the outer member. The replaceable handle includes an outer elongated housing with a passage having external or lateral communication extending longitudinally at least partially therealong from the distal end thereof. The distal end portion of the handle assembly defines an arrangement for securing an outer member of the medical device against lateral and axial movement. The handle also includes an inner elongated housing positioned in the outer housing central passageway and preferably extending proximally therefrom and preferably having a positioning cam channel arrangement for cooperating with a cam follower of the outer housing, for advantageously controlling the longitudinal and the rotational or circumferential movement of the inner housing with respect to the outer housing. The inner housing also includes a locking arrangement disposed therein and communicating with an inner passageway for receipt therein of the inner medical device member in a manner that controls axial movement thereof and also is manually actuatable to release the inner member for removal from the handle assembly.

One aspect of the invention is a replaceable, medical device handle for loading the proximal end of a medical device including first and second coaxial members and for controlling relative axial movement of the first and second coaxial members. The replaceable, medical device handle comprises an outer elongated housing having a distal end, a passage extending longitudinally therealong and having external communication thereto, and also a first attachment mechanism associated with the outer elongated housing for attaching the outer elongated housing to one of the first and second coaxial members when the proximal end of the medical device is in the passage for constraining the one of the first and second coaxial members against axial movement relative to the outer elongated housing. The medical device also comprises an inner elongated member position in said passage and extending therealong supported for axial movement relative to the outer elongated housing, and a second attachment mechanism associated with the inner elongate member for attaching the inner elongate member to the other of the first and second coaxial members when the proximal end of the medical device is in the passage for constraining the other of the first and second coaxial members against axial movement relative to the inner elongated member. The outer housing and the inner member include a projection positionable in an associated channel arrangement to achieve relative rotational and longitudinal movement of the first and second device members. The medical device also includes a spring operably coupled between the outer elongated housing and the inner elongated member for biasing the outer elongated housing and the inner elongated member toward a particular relative longitudinal position.

In one aspect of the invention, the locking arrangement includes a push button that is depressible to align a wide slot portion with the inner passageway to permit the proximal end of the inner medical device member to be inserted therethrough; release of the push button permits the button to be biased outwardly to align a narrow slot portion with the inner passagway, thus trapping an enlarged end of the inner medical device member proximally of the push button and permitting manipulation of the inner housing of the handle to move the inner medical device member.

In another aspect, a slotted end cap is affixed at the distal end of the outer housing, and a slotted insert is positioned inwardly from the end cap, with the outer medical device member insertable through a wide slot entrance along the side of the outer housing to be disposed in and along the slots to be aligned with the inner passageway of the inner housing. Rotation of the inner housing at its proximal end in turn rotates the insert within the outer housing, which misaligns a narrow portion of the slot of the insert with respect to the narrow slot of the end cap, thus trapping the outer medical device member against lateral movement, while the misaligning of the slots also defines stops for the outer medical device member against axial movement thereof when larger diameter portions thereof outside of the slots abut orthogonal faces of the end cap and insert at ends of the narrow slots.

In a further aspect of the present invention, the handle assembly includes a biasing arrangement to urge the inner housing proximally with respect to the outer housing, and thus urge the inner medical device member proximally with respect to the outer medical device member. This enables the inner member to be biased proximally with respect to the outer member without manual assistance. Where the medical device is a stone retriever, after the stone is captured by a stone basket of an inner control rod, the stone is securely held during withdrawal of the medical device from the patient without manual assistance to maintain the inner control rod biased proximally with respect to the outer cannula, thus allowing stone retrieval using only one hand to generally hold the handle assembly.

BRIEF DESCRIPTION OF THE DRAWINGS

An embodiment of the invention will now be described by way of example with reference to the accompanying drawings in which:

FIGS. 1 and 2 are isometric views of an assembly of the present invention of a stone retriever having a removable handle, with FIG. 1 showing the retriever in a first condition prior to capture of a stone, and FIG. 2 showing the retriever in a second condition following stone capture;

FIGS. 3 and 3A are an exploded view showing the components of the stone retriever and the handle;

FIG. 4 is a pictorial view of the push button;

FIG. 5 is a longitudinal cross-section view of the inner housing with the push button assembled therein;

FIG. 6 is an enlarged longitudinal cross-section view of the proximal end of inner housing showing the push button in a depressed position for insertion of the control rod of the stone retriever therethrough;

FIG. 7 is a pictorial view of the insert;

FIG. 8 is an enlarged longitudinal cross-section of the distal end of the outer housing to receive thereinto the insert and end cap;

DETAILED DESCRIPTION

Figure 9:
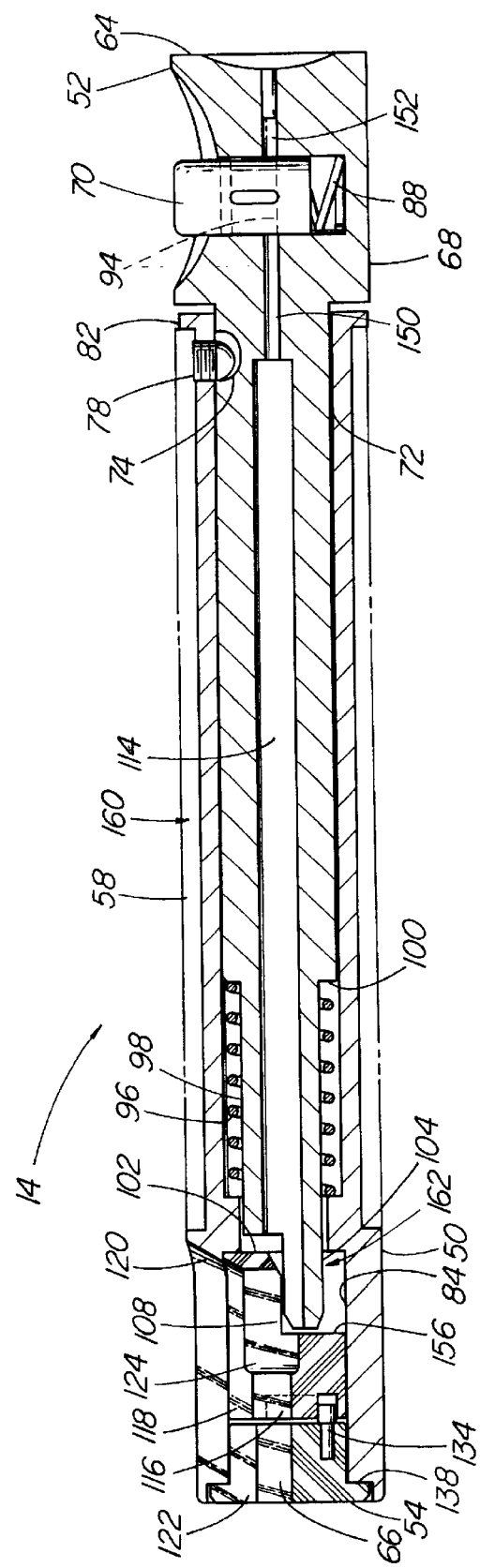
FIG. 9 is a longitudinal cross-section view of the assembled handle assembly of the present invention.

FIGS. 1 and 2 depict assembly 10 having a preferred illustrative embodiment of a replaceable handle 14 for a medical device 12 such as a stone retriever having a stone basket 16, which is used to remove a kidney stone 18 or calculus from the calix of a patient's kidney or the ureter leading therefrom. The replaceable handle 14 can likewise be utilized with other medical devices such as graspers, snares, retrievers, papillotomes, biopsy devices, occluders, tip deflecting wire guides, and other devices that are commonly used in conjunction with or through an operating lumen of an endoscope. Each of these medical devices is characterized in having at least two adjacent members at the proximal end thereof which are at least longitudinally and/or rotatably movable with respect to each other for the operation of the device at the distal end thereof.

By way of example, medical device 12 depicted in FIGS. 1 and 2 includes a stone basket 16 at the distal end of an inner control rod member or wire 22, the stone basket being defined by a plurality of self-expanding loops 20 (such as of nitinol) and which are collapsible for complete or at least partial retraction into outer sheath member or cannula 24 via relative longitudinal movement of inner control rod 22. The inner control rod 22 is attached to stone basket 16 and controls the extension of the stone basket from, and its retraction into, the distal end 26 of outer cannula 24. Since these endoscopic instruments are typically inserted through an operating lumen of an endoscope, the outer diameter of outer cannula 24 typically ranges from 1.0 French up to and including 10 French (0.33 mm to 3.3 mm) with the preferred range being from 2.0 French to 5.0 French (0.67 mm to 1.67 mm). Inner control rod 22 extends through the passage of outer cannula 24 and does not exceed the outer diameter of the outer cannula except, for example, distal stop 36 (FIG. 3). Once a stone 18 is captured within loops 20, inner control rod 22 is movable proximally to retract loops 20 into outer cannula distal end 26 until stopped by the presence of the stone 18 captured within the loops.

Handle assembly 14 includes an outer housing 50, an inner housing 52, end cap 54, insert 56, and hand grip 58. The end cap 54 and insert 56 are secured in and along a central passageway within the distal end portion 60 of the outer housing 50, distally of the distal end of inner housing 52. The proximal end portion of the stone retriever extends into distal end 62 of the handle assembly and extends toward the proximal end 64 thereof, with the stone retriever being disposed within and along a narrow-width slot 66 at the distal end 62. Inner housing 52 includes a locking assembly 69 (FIG. 6) within its proximal end portion 68 that secures the proximal end portion 32 of inner control rod member 22 sufficiently to move the inner control member 22 axially with the inner housing 52. When the handle assembly is in the condition shown in FIG. 1, push button 70 can be depressed to unlock inner control rod 22 from the locking arrangement; stone retriever 12 can then be removed by manually lifting upwardly (e.g., on the gripping sleeve 28) to raise the outer cannula 24 upwardly in narrow width slot 66 and outwardly therefrom, and then pulling the stone retriever distally, completely removing it from handle assembly 14.

When the inner control rod 22 is secured by the locking assembly 69, inner control rod 22 is controllably movable within outer cannula 24 by manipulation of the inner housing 52 with respect to the outer housing 50, of handle assembly 14. As seen in FIG. 2, the outer housing 50 is first rotated a quarter turn with respect to the inner housing 52, whereafter the inner housing 52 is moved relatively axially in the proximal direction with respect to the outer housing 50, and carries inner control rod member 22 proximally therewith as outer cannula 24 is held within distal end portion 60 (see FIGS. 3 and 10) against any substantial axial movement in either direction. Insert 56 is keyed to the distal end of the inner housing, and remains in substantially the same angular orientation as the inner housing, while outer housing 50 and end cap 54 are rotated together. Also seen in FIG. 2 is a portion of the shaft 72 of the inner housing 52 extending distally from the proximal end portion 68. Defined in shaft 72 are a circumferential cam channel 74 and axial cam channel 76 extending distally therefrom, that cooperate with a cam follower 78 (see FIGS. 3 and 9) in the outer housing 50.

Reference is now made to FIGS. 3 and 3A, in which all the components of the stone retriever and the handle assembly are seen. Cam follower 78 is threaded into an aperture 80 into outer housing 50 that is adjacent to flange 82, until it protrudes into central passageway 84 and into either one of cam channels 74, 76 of inner housing shaft 72 upon full assembly. Upon complete handle assembly, hand grip 58 is disposed between distal end portion 60 and flange 82 and covers cam follower 78 and aperture 80; hand grip 58 preferably comprises an elastomeric material in a tight fit around outer housing 50. Push button 70 is seated in a transverse hole 86 and is biased outwardly by a spring 88; a pair of lock pins 90 secure the push button within hole 86 and extend into and ride along grooves 92 that permit limited transverse movement of push button 70. Push button 70 also includes a through-slot 94 through and beyond which will extend the proximal portion 32 of inner control rod 22 of the stone retriever 12, as may be discerned in FIG. 6.

Figure 10:
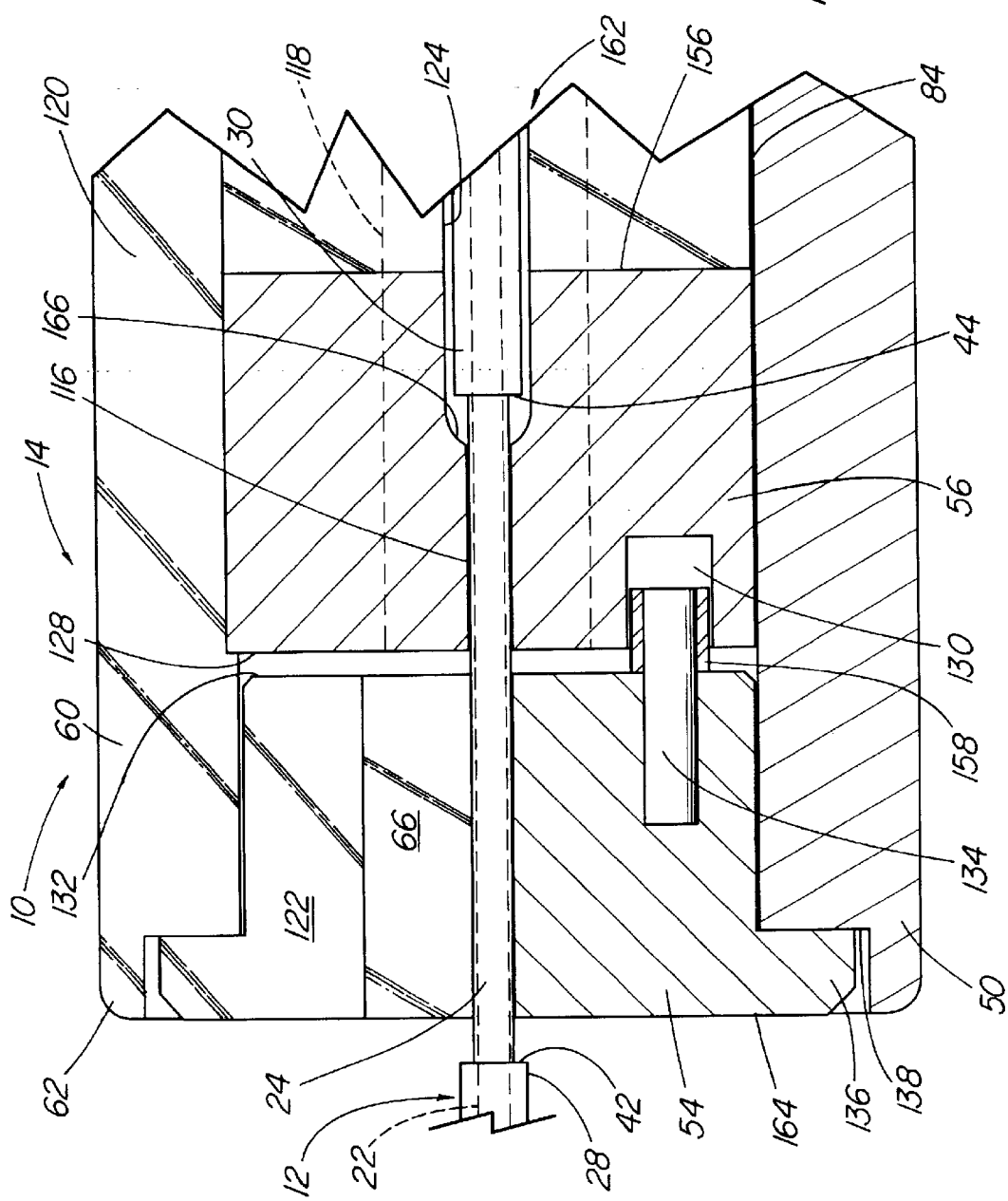
FIG. 10 is an enlarged sectioned view of the distal end of the assembly of FIG. 2 illustrating the relationship of the stone retriever and the distal portion of the handle assembly to limit the movement of the outer cannula.

A compressible coil spring 96 will be disposed around reduced diameter forward shaft portion 98 of inner housing 52 upon assembly, and will be biased between forwardly facing abutment surface 100 of shaft 72 and collar 102 within central passageway 84 of outer housing 50, as seen in FIG. 9. A first key 104 is defined at the distal end 106 of shaft 72 and has the shape of a semicircle in cross-section, to cooperate with a second key 108 defined at the proximal end 110 of insert 56, also semicircular in cross-section. A groove 112 is seen along first key 104 aligned with inner passageway 114 of inner housing 52, that in cooperation with second key 108 will define a nest 162 (as shown in FIGS. 9 and 10) for the distal end of larger diameter sleeve portion 30 of outer cannula 24 to prevent axial movement of outer cannula 24 distally from handle assembly 14, after assembly of stone retriever 12 to handle assembly 14. First and second keys 104,108 also cooperate to assure that insert 56 is rotated upon rotation of inner housing 52 when the inner housing is in its distal-most condition (FIG. 1), following cam channel 74.

Insert 56 includes a narrow width slot portion 116 that aligns with slot 66 of end cap 54, and further includes a tapered slot entrance 118 that will complement tapered slot entrance 120 of outer housing 50. End cap 54 also includes a tapered slot entrance 122 that also complement slot entrance 120 of outer housing 50. The generous tapered slot entrances 118, 122 will facilitate insertion of stone retriever 12 when assembled to handle assembly 14. In insert 56, a wider slot portion 124 extends proximally from narrow width slot 116 and will open onto key face 126 (best seen in FIGS. 7 to 10) opposed from groove 112 of first key 104 to complete the nest 162 for outer cannula sleeve portion 30 (FIG. 9). Distal end face 128 of insert 56 includes defined thereinto a guide channel 130 that extends arcuately for about 90°. Proximal end face 132 of end cap 54 includes a small diameter cylindrical boss 134, such as a stylet pin press-fit into an aperture of end cap 54, that upon handle assembly extends into guide channel 130 of insert 56, preferably in a snug fit by reason of a compressible coating 158 on boss 134, such as nylon tubing. Flange 136 of end cap 54 will seat against a shoulder within a recess 138 at the distal end 62 of outer housing 50, and preferably end cap 54 is affixed to outer housing 50 such as by adhesive. Outer housing 50, inner housing 52, end cap 54, insert 56 and push button 70 may all be molded for example of Delrin plastic material, although the suitability numerous other materials will be apparent to those of routine skill in the art. The slotted end cap 54 and the slotted insert 56 can alternatively be fixed to the distal end of the inner housing of the handle. In such an embodiment the distal end portion of the inner housing of the handle would not need to be slotted and the combination of the distal end of the first part, the end cap, and the "insert" would be considered to be the end portion of the inner housing. The insert would require a relatively fixed and slotted outer sleeve relative to which the inner part of the "insert" could be rotated for locking and unlocking purposes. The outer sleeve could be part of the end cap or part of the said first part of the handle. The slot in the inner housing can extend over only the distal portion thereof or can extend over a greater portion or along the entire length thereof.

Also shown in FIG. 3, inner control rod 22 of stone retriever 12 includes an enlarged proximal end 34 that terminates rod proximal portion 32, and further includes a collar 36 spaced forwardly from proximal end 34. Collar 36 abuts the proximal end 38 of outer cannula 24 to prevent the collar 36 from passing into the outer cannula 24, while enlarged proximal end 34 cooperates with the locking arrangement defined in proximal end portion 68 of inner housing 52 to secure the stone retriever to the handle assembly. Enlarged proximal end 34 will be disposed proximally of through-slot 94 of push button 70 upon assembly of the stone retriever to the handle assembly. Preferably, portions of outer cannula 24 include plastic material integrally bonded thereto, including gripping sleeve 28, sleeve portion 30 and sleeve portion 40 adjacent to proximal cannula end 38, respectively.

FIGS. 4 to 6 illustrate the locking arrangement of stone retriever 12 by handle assembly 14, in proximal end portion 68 of inner housing 52. Push button 70 includes a spring-receiving recess 140, adapted to receive thereinto a portion of spring 88 when secured in hole 86 of inner housing 52. Through-slot 94 of push button 70 is shaped like a keyhole in cross-section with a widened upper portion 142 and a narrow lower portion 144; upper portion 142 is sufficiently large to receive therethrough enlarged proximal end 34 of inner control rod 22, while lower portion 144 is narrower than proximal control rod end 34 but slightly larger than proximal end portion 32 of the inner control rod. Ergonomic recess 146 in proximal end portion 68 of inner housing 52 enables depression of push button 70 into hole 86 sufficiently to compress spring 88 against hole bottom 148. Inner passageway 114 of inner housing 52 includes a small diameter portion 150 within proximal end portion 68 that intersects hole 86 to include a proximal passageway portion 152; preferably, a plug member 154 such as a stylet pin is utilized to close off passageway portion 152, at proximal end 64 by being press-fit into the passageway exit. Alternatively, the passageway portion 152 could be made to terminate prior to reaching the proximal end 64. Passageway portions 150,152 need only be large enough for the proximal end portion 132 of inner control rod 22 and its enlarged end 34 and collar 36; passageway 114 is sufficiently large in diameter to receive therealong outer cannula 24 and sleeve portions 40,42.

As seen in FIG. 5, when push button 70 is undepressed, small width lower slot portion is aligned with passageway portions 150,152. As seen in FIG. 6, when push button 70 is fully depressed, wider upper slot portion 142 becomes aligned with small diameter passageway portions 150,152 enabling enlarged proximal end 34 of inner control rod 22 to be moved axially through, the through-slot 94 during either insertion or removal. Upon full insertion through through-slot 94, enlarged proximal end 34 resides beyond push button 70 in proximal passageway portion 152 adjacent to plug 154, and upon release of push button 70, enlarged proximal end 34 is locked in proximal passageway portion 152 thus locking the inner control rod 22 in handle assembly 14. Guide channels 92 along either side of push button 70 assure that push button movement is limited by lock pins 90, and is also secured in hole 86 of inner housing 52, and is retained in an appropriate angular orientation within hole 86 to maintain through-slot 94 in an axial orientation to be aligned with passageway portions 150,152.

FIGS. 7 and 8 illustrate greater detail of end cap 54, insert 56 and distal end portion 60 of outer housing 50. FIG. 7 is a pictorial view of insert 56 to show the larger width slot 124 proximally from narrow width slot 116, and the opening onto the bottom face 126 of second key 108 proximally of surface 156 that is orthogonal to bottom face 126. In FIG. 8 end cap 54 and insert 56 are received into distal end portion 60 of outer housing 50, into passageway 84, with flange 136 being bonded into recess 138 at distal end 62 of the outer housing, thus securing insert 56 within outer housing 50 distally of collar 102. Boss 134 extends proximally from proximal end face 132 of end cap 54 to be received into guide channel 130 in a snug fit. Outer housing 50 also is seen to include a recess 160 along its outer surface proximally from distal end portion 60, for receipt thereinto hand grip 58.

Referring to FIG. 9, handle assembly 14 is shown in cross-section and shows inner housing 52 assembled within outer housing 50, compressing spring 98 between collar 102 and distally facing surface 100 of shaft 42. Cam follower 78 is affixed in position within aperture 80 adjacent to flange 82 of outer housing 50, and protrudes into inner passageway 84 and into circumferential cam channel 74 along shaft 42 (see FIGS. 2 and 3). Circumferential cam channel 74 may include a detent portion at its end opposite the axial cam channel 76, the detent portion extending slightly distally to provide a detent when engaged by the cam follower at the position shown. First key 104 at distal end 106 of inner housing 52 is opposed from second key 108 of insert 56, such that groove 112 is opposed from wide slot portion 124 of insert 56 proximally of surface 156. Narrow slot portions 66,116 of end cap 54 and insert 56 are radially aligned, as are slot entrances 122,118,120 of end cap 54, insert 56 and outer housing 50, and communicate with groove 112 of key 104 and inner passageway 114 of inner housing 52, and thus handle assembly 14 is fully assembled and ready to receive stone retriever 12, for proximal end 34 of inner control rod 22 to extend fully through inner passageway 114, small diameter passageway portion 150, and also through through-slot 94 and passageway portion 152 when push button 70 is fully depressed as in FIG. 6.

Handle assembly 14 limits movement of the outer cannula 24, as shown in FIG. 10; the distal portion of the handle assembly corresponds to the arrangement of FIG. 2 wherein the inner housing has been rotated a quarter-turn with respect to outer housing 50 and correspondingly has rotated insert 56 as well by reason of the relationship of first key 104 of inner housing 52 with second key 108 of insert 56 (see FIGS. 3 and 9). The rotational movement misaligns narrow width slot 66 of end cap 54 with narrow width slot portion 116 of insert 56 such that the outer cannula 24 of stone retriever 12 is now trapped against any radial movement. The width of both narrow width slot 66 and narrow width slot portion 116 is selected to be just incrementally larger than the diameter of outer cannula 24, and the outer diameter of sleeve portions 30,40 and gripping sleeve 28 is selected to be substantially larger than the width of slot 66 and slot portion 116. It can be seen that the proximal end of gripping sleeve 28 defines a stop edge 42 that is abuttable with distal face 164 of end cap 54 to prevent further proximal movement of the outer cannula; similarly, the distal end of sleeve portion 30 defines a stop edge 44 that is abuttable with channel end 166 of wider slot portion 124 of insert 56 to prevent further distal movement of the outer cannula. Thus, inner control rod 22 can be assuredly moved axially relative to outer cannula 24, by appropriate manipulation of inner housing 52 axially with respect to outer housing 50.

The replaceable medical device handle of the present invention advantageously provides for easy side loading of the proximal end of a medical device and fixation thereto. This side-loading feature is a convenience to the physician and is readily appreciated, particularly, when a grasper or stone basket can not be operated to release the captured stone, tissue sample or other device fragment. Should the captured stone become unreleasable, replaceable handle 14 can be easily removed from the proximal end of the medical device so as to permit the endoscope to be removed from the patient and passed over the proximal portion of the medical device. This advantageously eliminates the destructive removal of the handle or an enlarged proximal end from the medical device prior to removal of the endoscope therearound. The replaceable handle 14 is then easily reattached to the proximal end of the medical device for subsequent operation and removal of the medical device by the attending physician.

What is claimed is:

1. A handle for loading and controlling relative axial movement of the first and second coaxial members of a medical device, the handle comprising:

an outer elongated housing having a distal end, a passage extending longitudinally therealong and having external communication thereto, and an end cap with a boss and a coating at a proximal end of the end cap, and further comprising a first attachment mechanism for attaching the outer elongated housing of the first coaxial member when the proximal end of the medical device is in the passage for constraining the first coaxial member against axial movement relative to the outer elongated housing;

an inner elongated member positioned in said passage and extending therealong supported for axial movement relative to the outer elongated housing, and an insert slotted to accommodate the boss, and further comprising a second attachment mechanism for attaching the inner elongate member to the second coaxial member when the proximal end of the medical device is in the passage for constraining the second coaxial member against axial movement relative to the inner elongated member;

the outer housing and the inner member including a projection positionable in an associated channel arrangement to achieve relative rotational and longitudinal movement of the first and second device members; and a spring operably coupled between the outer elongated housing and the inner elongated member for biasing the outer elongated housing and the inner elongated member toward a particular relative longitudinal position.

2. A handle according to claim 1, wherein channels of the channel arrangement are formed on an outer surface of the inner member, and the projection is fixed to the outer housing and is arranged to be movable in the channels.

3. The handle of claim 1, wherein said positioning channel comprises a longitudinal segment and a lateral segment.

4. The handle of claim 3 wherein the lateral segment of the positioning channel includes a detent for retaining the projection within the lateral segment of the positioning channel.

5. The handle of claim 1, wherein said projection extends into said positioning channel.

6. The handle of claim 1, wherein said first attachment mechanism includes a collar rotatably positioned in said passage about said distal end of said outer elongated housing and having a slit with external communication extending longitudinally therethrough and communicating with said passage.

7. The handle of claim 6, wherein said collar also has an offset recess and wherein said inner elongated member includes an offset projection extending distally and longitudinally therefrom and positionable in said offset recess of said collar for rotation of said collar in said passage.

8. The handle of claim 1, wherein said first attachment mechanism comprises a cap fixedly positioned about said distal end of said outer elongated housing and having a slit with external communication extending longitudinally therethrough and communicating with said passage.

9. The handle of claim 8, wherein said first attachment mechanism includes a collar rotatably positioned in said passage about said distal end of said outer elongated housing and having a slit with external communication extending longitudinally therethrough and communicating with said passage.

10. The handle of claim 1 wherein the second attachment mechanism includes a push button having a longitudinal slot therein, the slot having a portion of larger transverse dimension for receiving an enlarged portion at the proximal end of the second coaxial member and a portion of smaller transverse dimension for retaining the proximal end of the second coaxial member.

11. The handle of claim 10 additionally comprising a spring operatively coupled to the push button for biasing the push button toward a position wherein the enlarged portion of the second coaxial member is engaged with the slot portion of smaller transverse dimension.

12. A medical device handle comprising:

an outer elongated housing having a distal end, a passage extending longitudinally therein and having external communication along a distal portion thereof, an end cap having a boss and a compressible coating at the distal end, and a first attachment mechanism disposed about said distal end and communicating with said passage for receipt of a first medical device member therein;

an inner elongated member having an insert with a slot for accommodating the boss, the inner elongated member positioned in said passage and extending proximally therefrom and having a positioning channel, a second attachment mechanism disposed therein and communicating with said passage for receipt therein of a second medical device member adjacent the first medical device member, said outer elongated housing also including a projection positionable into said positioning channel, said inner elongated member being longitudinally slidable in said passage when said projection is positioned in a first component of said positioning channel and being rotatable in said passage when said projection is positioned in a second component of said positioning channel; and a spring operatively coupled between the outer elongated housing and the inner elongated member whereby the inner elongated member is biased toward one of the distal end of the outer elongate housing and a proximal end of the outer elongated housing when the projection is positioned in the first component of the positioning channel.

13. The handle of claim 12, wherein said first component of said positioning channel comprises a longitudinal segment of said positioning channel and wherein said second component of said positioning channel comprises a lateral segment of said positioning channel.

14. The handle of claim 12, wherein said projection extends into said positioning channel.

15. A handle for supporting therein a medical device with inner and outer members, the handle comprising:

a first part with a slotted section extending over at least a distal end portion of the first part and an end cap with a boss at the distal end;

a second part having a distal end with a slotted insert accommodating the boss, and at least one section axially movable within the first part;

a spring biasing the first and second parts in opposite longitudinal directions;

wherein the distal end portion of the first part comprises an arrangement for securing the outer member of the device against lateral and axial movement;

wherein the second part comprises a mechanism for controlling axial movement of the inner member relative to the outer member; and wherein the arrangement is designed to also permit lateral movement of the outer member, and the mechanism is designed to be able to also release the inner member whereby the medical device can be withdrawn from the handle via the slotted section.

* * * * *